(12) United States Patent
Machado et al.

(10) Patent No.: US 9,931,174 B2
(45) Date of Patent: Apr. 3, 2018

(54) GLOVE DISPENSER

(71) Applicants:Camilo Machado, Novi, MI (US);
Javier Ramirez, Novi, MI (US);
Cutberto Medina, Novi, MI (US);
Sergio Nevarez, Livonia, MI (US)

(72) Inventors: Camilo Machado, Novi, MI (US);
Javier Ramirez, Novi, MI (US);
Cutberto Medina, Novi, MI (US);
Sergio Nevarez, Livonia, MI (US)

( * ) Notice: Subject to any disclaimer, the term of this patent is extended or adjusted under 35 U.S.C. 154(b) by 0 days.

(21) Appl. No.: 14/751,693

(22) Filed: Jun. 26, 2015

(65) Prior Publication Data

US 2015/0374441 A1   Dec. 31, 2015

Related U.S. Application Data

(60) Provisional application No. 62/018,055, filed on Jun. 27, 2014.

(51) Int. Cl.
*B65H 5/28* (2006.01)
*G07F 11/68* (2006.01)
*A61B 42/40* (2016.01)
*A61B 50/20* (2016.01)
*A61B 17/00* (2006.01)
*A61B 50/10* (2016.01)

(52) U.S. Cl.
CPC .............. *A61B 42/40* (2016.02); *A61B 50/20* (2016.02); *A61B 2017/00398* (2013.01); *A61B 2017/00734* (2013.01); *A61B 2050/105* (2016.02)

(58) Field of Classification Search
CPC .... A47K 2210/02; A61B 42/40; A61B 50/20; A61B 205/105; A61B 2017/8734
USPC ............................................... 221/73, 25, 56
See application file for complete search history.

(56) References Cited

U.S. PATENT DOCUMENTS

| | | | | |
|---|---|---|---|---|
| 3,675,664 A | * | 7/1972 | Kitowski | ................ B60R 7/087 248/311.2 |
| 4,032,038 A | * | 6/1977 | Hendricks | ............. B65B 43/123 221/71 |
| 4,425,012 A | * | 1/1984 | Kley | ...................... A47K 10/24 211/105.3 |
| 4,773,532 A | | 9/1988 | Stephenson | |
| 5,065,894 A | * | 11/1991 | Garland | ................ A61F 15/002 221/25 |
| 5,301,634 A | * | 4/1994 | Ho | ........................ A01K 39/012 119/477 |
| 5,674,350 A | * | 10/1997 | Jurgich | ..................... B65C 3/12 156/540 |

(Continued)

FOREIGN PATENT DOCUMENTS

EP         0 542 332 B1    12/1997

*Primary Examiner* — Rakesh Kumar
(74) *Attorney, Agent, or Firm* — Fay Sharpe LLP; James E. Scarbrough

(57) ABSTRACT

A glove dispenser has a housing having first and second opposed walls. A glove roll is disposed within the housing for carrying a roll of removable gloves. An electro-mechanical feed mechanism rotates the roll. One or more proximity sensors are positioned within the housing to detect a user's hand and activate rotation of the glove roll. Activators are located on the housing first and second wall which activate the roll to rotate to dispense a glove from the roll. A take-up roll can be provided for receiving roll material after the gloves are dispensed.

7 Claims, 11 Drawing Sheets

(56) References Cited

U.S. PATENT DOCUMENTS

| | | | |
|---|---|---|---|
| 5,791,586 A * | 8/1998 | Cayford | B05B 15/0456 242/571.4 |
| 5,960,995 A * | 10/1999 | Leatherman | B67D 1/16 137/313 |
| 6,271,872 B1 * | 8/2001 | Nagata | B41J 2/325 347/171 |
| 6,375,034 B1 | 4/2002 | Corbett | |
| 6,698,743 B2 * | 3/2004 | Kuramoto | B42C 9/0068 270/58.08 |
| 6,805,262 B1 * | 10/2004 | Frazier | A47K 5/1214 221/96 |
| 7,077,289 B2 * | 7/2006 | Ross | A61F 15/002 221/225 |
| 7,350,553 B2 * | 4/2008 | Yu Chen | B29C 63/0013 156/526 |
| 7,635,067 B1 | 12/2009 | Flynn | |
| 7,712,642 B2 * | 5/2010 | Gaines | A47G 25/904 223/111 |
| 7,731,056 B2 | 6/2010 | Tramontina | |
| 7,793,608 B1 * | 9/2010 | Udouj | B65H 18/28 116/200 |
| 8,360,273 B2 * | 1/2013 | Reinsel | A47F 1/10 211/49.1 |
| 8,398,041 B2 * | 3/2013 | Brinkdopke | F16B 45/02 248/316.1 |
| 8,485,860 B2 * | 7/2013 | Oliver | B24B 21/04 451/10 |
| 8,528,779 B2 * | 9/2013 | Hamer | B65D 75/42 221/71 |
| 9,295,344 B2 * | 3/2016 | Reinsel | A47F 1/10 |
| 2005/0199690 A1 * | 9/2005 | Peterson | B65D 5/0254 229/122.1 |
| 2005/0206715 A1 * | 9/2005 | Sasaki | B41J 11/0075 347/221 |
| 2006/0096999 A1 * | 5/2006 | Horng | B65C 9/1865 221/73 |
| 2006/0118567 A1 * | 6/2006 | Linnebur | A47K 10/421 221/45 |
| 2006/0249240 A1 * | 11/2006 | Dijkstra | B65C 9/1884 156/64 |
| 2007/0145062 A1 * | 6/2007 | Formon | G07F 11/66 221/30 |
| 2007/0187949 A1 * | 8/2007 | Uruno | G09F 3/0288 283/105 |
| 2009/0029628 A1 * | 1/2009 | Oliver | B24B 21/04 451/5 |
| 2009/0036027 A1 * | 2/2009 | Rossignol | B24B 21/04 451/5 |
| 2010/0018987 A1 * | 1/2010 | Hamer | B65D 83/0454 221/25 |
| 2010/0078459 A1 * | 4/2010 | Reinsel | A47K 10/36 225/10 |
| 2010/0089939 A1 * | 4/2010 | Morris | A47K 10/36 221/1 |
| 2010/0170915 A1 * | 7/2010 | Reinsel | A47F 1/10 221/279 |
| 2011/0000620 A1 * | 1/2011 | Dijkstra | B41J 3/4075 156/361 |
| 2012/0183341 A1 * | 7/2012 | Takahashi | B41J 2/325 400/225 |
| 2012/0273434 A1 * | 11/2012 | Niederhuefner | A47F 1/128 211/4 |
| 2013/0155131 A1 * | 6/2013 | Izawa | B41J 11/46 347/5 |
| 2013/0175289 A1 * | 7/2013 | Sternberg | B65C 9/1869 221/70 |
| 2013/0175418 A1 * | 7/2013 | Sternberg | B65C 9/00 248/301 |
| 2015/0097068 A1 * | 4/2015 | Larson | A47K 10/36 242/563 |
| 2015/0374441 A1 * | 12/2015 | Machado | A61B 50/20 221/2 |

* cited by examiner

GLOVE DISPENSER

CLAIM OF PRIORITY

This application claims priority from Provisional Application Ser. No. 62/018,055, filed on Jun. 27, 2014, the entirety of which is hereby incorporated by reference.

BACKGROUND OF THE DISCLOSURE

The disclosure relates to a glove dispenser. Specifically, it relates to an electro-mechanized glove dispenser for dispensing gloves for use in surgical, medical, or dental applications, but is not limited to those applications.

Individuals in the health care or dental industry regularly don disposable gloves in order to prevent the transmission of bacteria or other contaminants to themselves and to patients. In certain cases, the disposable gloves are typically contained within, and dispensed from, a box or container. When donning a pair of gloves dispensed in this manner, a user typically grasps a glove and pulls the glove from the box using an uncovered hand. Once removed from the box, the user places the glove onto one of his uncovered hands. The user can then use his now covered hand to grasp and remove a second glove from the box and then place the second glove upon his ungloved hand. This of course affects the sterility of the gloves which may contaminate the gloves and cause potential issues for the patent or glove wearer.

There are also a number of dispensing devices which are well known for dispensing and cutting webs or rolls of material such as paper toweling. With such dispensers, the process of dispensing and cutting the material is carried out automatically by a user pulling on the free end of the material that extends from a dispensing slot in the apparatus. In a typical configuration, the web material is engaged against a rough friction enhancing surface of a feed drum and the action of pulling the web tail causes the drum to rotate. The drum includes a drive mechanism and, after the initial pull on the web tail by a user, the drum is driven a predetermined rotational degree to dispense a metered amount of the material. These types of dispensers are commonly referred to as "no-touch" or "sanitary" dispensers because the user does not manually operate any portion of the drive or cutting mechanism. The user only touches the tail end of the material.

There is a need for a glove dispenser which utilizes the "no touch" concept discussed above for dispensing gloves by using a roll system of gloves activated by a proximity sensor and a mechanism of dispensing of gloves based on a rotation engine which an electric motor driven by an electronic circuit fed by a battery bank or any electric power supply. The rotation engine can also be driven by the movement of a knob or similar manual device. Gloves are thereby dispensed from a roll at the bottom of the dispenser. The roll of gloves can be replaced on either the side or on the top of the cover.

Thus, there is a need for a glove dispenser which overcomes the above-mentioned difficulties and others while providing better and more advantageous results.

SUMMARY OF THE DISCLOSURE

The disclosure relates to a glove dispenser. More particularly, it relates to an electro mechanized glove dispenser for dispensing gloves for use in surgical, medical, or dental applications, but is not limited to those applications.

By contrast to conventional glove dispensers, embodiments of the present disclosure relate to a system for dispensing gloves, such as disposable polymer or latex film gloves of the type used in the dental or medical industry. The glove dispensing system includes glove bearing sheets and a glove opening mechanism. In use, the glove dispensing system has a dispensing end whereby rolls carrying the glove bearing sheets presents the gloves to a user. As such, the glove dispensing system provides the user with a substantially sterile glove in a manner that allows the user to easily don the gloves while limiting a risk of the user contaminating an exterior surface of the glove by touching with his hands or other body parts.

In one embodiment of the disclosure, the gloves are removably applied to the sheets such as by adhesive or Velcro®-like hook and loop fasteners. Alternatively, the gloves can be integrally formed as part of the sheets.

In another embodiment, a series of perforations may extend about the outer periphery of the glove, that secures the gloves to the sheets and that allows ease of removal of the gloves from the sheets after being donned by the user.

According to another embodiment of the disclosure, a glove dispensing system includes a housing, a glove bearing sheet carried by the housing, and a glove opening mechanism coupled to the housing.

Another embodiment of the disclosure is a glove dispenser which includes a roll of gloves activated by a proximity sensor. Once the proximity sensor is activated, a battery operated or electric rotation engine acts as the mechanism for dispensing the gloves. The dispenser further features a cover or housing which allows access to the roll of gloves in order to replace the glove roll.

In accordance with another embodiment of the disclosure, a glove dispenser is manually activated by a mechanism on the cover or housing in order to dispense the gloves at the bottom of the dispenser.

According to another embodiment of the disclosure, the dispenser includes a housing of any appropriate shape or configuration.

In accordance with another embodiment of the disclosure, a roll is disposed in a housing for rotationally carrying a roll of removable gloves. The roll can be of various materials, such as silk, paper, a plastic film, etc. The gloves themselves can be mounted or placed on the roll of material.

In accordance with another embodiment of the disclosure, a dispensing slot is defined and formed at a bottom of the housing through which the sheets of gloves are dispensed. A specific length of the material extends out of the dispensing slot and defines an end portion that a user grasps and pulls in order to dispense the gloves from the material.

In accordance with another embodiment of the disclosure, an electromechanical feed mechanism is disposed in the housing through which the roll material passes in its running path through the dispenser.

In accordance with another embodiment of the disclosure, three separate rolls can be mounted spaced apart in parallel in a housing, wherein a first roll contains small sized gloves, a second roll contains medium sized gloves and a third roll contains large size gloves.

In accordance with another embodiment of the disclosure, a housing for the glove dispenser can include a removable or rotatable plastic cover housing a roll of gloves, a pressing bar or roll, a lower roll mechanism of a pair of rolls through which the roll material presses, and a proximity sensor mounted at the bottom of the housing.

In accordance with another aspect of the disclosure, rollers may apply pressure to the glove roll material and the material may be manually pulled through the rollers to dispense the gloves.

In accordance with another embodiment of the disclosure, the roll of gloves may include gloves which are folded in half. The folded gloves are stored or placed on rolls.

In accordance with another embodiment of the disclosure, a glove sensor is needed to detect a set of gloves has been dispensed from glove roll.

In accordance with another embodiment of the disclosure, an empty sensor is used so that the dispenser can detect that the glove roll is about to be finished or emptied.

According to another embodiment of the disclosure, the glove dispenser has a case or housing that contains two rolls, where each roll is held by a roll holder. Each roll is assembled over a stool. There is a tensor rod between the two rolls and a tenser holder. The device also has proximity sensor, a line counter sensor, two engines or motors, an area for batteries, a tray, a front door with two hinges, and a lock.

In accordance with a preferred embodiment of the disclosure, a glove dispenser has a housing having first and second opposed walls; a glove roll disposed within the housing for carrying a roll of removable gloves; an electro-mechanical feed mechanism for rotating the roll; proximity sensors positioned within the housing to detect a user's hand; and activators located on the housing first and second walls which activate the roll to rotate to dispense a glove from the roll.

In accordance with another embodiment of the disclosure, a glove dispenser has a glove roll having a sheet with gloves removably secured thereto; a conveyor belt driven by rollers wherein the glove roll rotates on the conveyor belt; a proximity sensor which senses a user's hand and activates a motor which drives the conveyor belt; and a pressing roll which presses the glove roll against the conveyor belt.

In accordance with another embodiment of the disclosure, a glove dispenser assembly has a housing; a glove dispenser; a glove roll mounted within the housing; the glove roll has roll materials wound thereon wherein gloves are removably secured to the roll material; a glove tray positioned at a bottom portion of the housing; a motor for driving the glove roll; a proximity sensor for detecting a user's hand; and a take-up roll positioned below the glove roll.

In accordance with another embodiment of the disclosure, a glove dispenser has a housing; a glove roll holding a roll of gloves removably secured to a sheet; a take-up roll positioned below the glove roll; a tensor arm for controlling movement of the glove roll and the take-up roll; at least one proximity sensor positioned near a lower portion of the housing; and a glove take-up tray positioned near a lower portion of the housing.

Still other aspects of the disclosure will become apparent upon a reading and understanding of the following detailed description.

DETAILED DESCRIPTION OF THE DISCLOSURE

Figure 1:
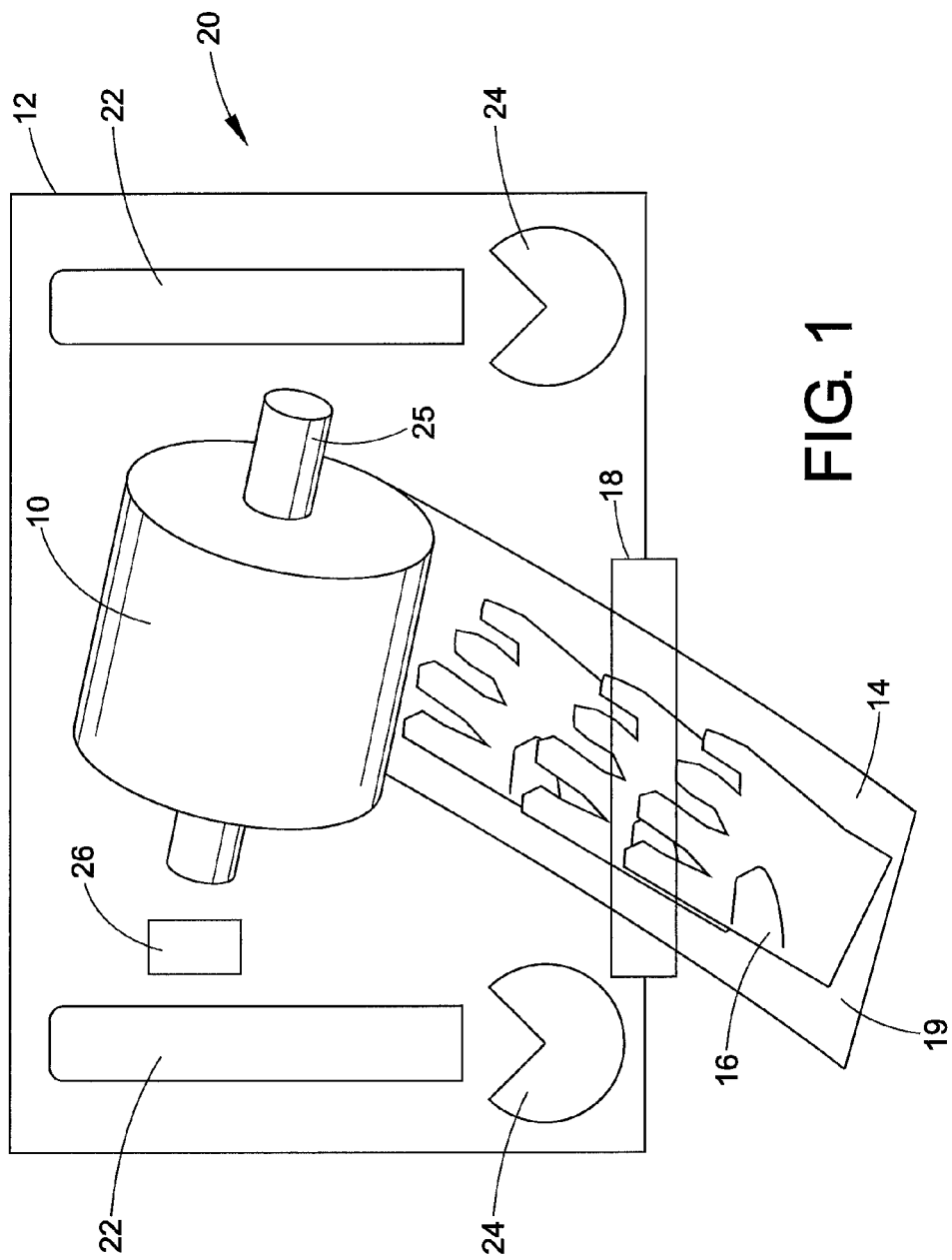
FIG. 1 is an isometric exploded view of a glove dispenser system, according to one embodiment of the disclosure.

The disclosure relates to a glove dispenser. Specifically, it relates to an electro-mechanized glove dispenser for dispensing gloves for use in surgical, medical, or dental applications, but is not limited to those applications. The dispenser includes a housing of any appropriate shape or configuration.

Referring now to FIGS. 1-7, a glove dispenser mechanism in accordance with a preferred embodiment of the disclosure is shown. A roll 10 of material is disposed in a housing 12 for rotationally carrying a roll of removable gloves 16. The roll material itself can be made of various materials, such as silk, paper, a plastic film, etc. The gloves themselves can be mounted or placed on the roll of material, or can be removably secured thereto such as by adhesive material or Velcro®-like hook and loop fasteners or can be perforated on the material sheet itself. A dispensing slot 18 is defined and formed at a bottom of the housing through which the sheets of gloves are dispensed. A specific length of the material extends out of the dispensing slot 18 and defines an end portion or tail 19 that a user grasps and pulls in order to dispense the gloves from the material.

An electro-mechanical feed mechanism 20 is disposed in the housing 12 which control rotation of the roll and through which the roll material passes in its running path through the dispenser. Specifically, proximity sensors 22 are positioned on opposing sides of the roll 10 to detect a user's hand within about a 5 cm to 10 cm range. Activators 24 are positioned on opposite sides of the roll below the sensors. The user places his/her hand under the activator which in turn activates the roll to rotate a predetermined amount thereby dispensing gloves from the roll.

The feed mechanism 20 may also have a mechanical mode of operation wherein measured sheets are dispensed by a user simply grasping and pulling on a tail end extending from the dispensing slot. This pulling action is not used in any way to build up energy or spring load a potential energy feed device or cutter of any sort. Thus, the pulling action meets with little resistance from the feed mechanism since the pull force is primarily the unwind resistance of the material roll.

The feed mechanism 20 preferably has an electrical operational state that is triggered to automatically drive the feed mechanism with an electrically powered motor to dispense a measured length of the paper material out of the dispensing slot to define the tail to be pulled by a user. The paper is rolled onto a separate roll that will be discarded when the roll of gloves is finished. A control circuit is configured with the motor and feed mechanism to automatically switch the feed mechanism between its operational states at the correct time in the dispensing sequence.

In one embodiment of the disclosure, the feed mechanism 20 includes a feed roller 25 drivingly engaged by a motor 26 in the second operational state. The feed roller holds the glove roll 10 and is freely rotatable in the first operational state to the extent that it does not impede a user from manually pulling a measured sheet of the glove roll from the dispenser. The feed roller 25 may be mechanically coupled to the motor 26 by any number of various configurations. For example, the motor may drive a small friction roll that engages the surface of the feed roller to rotate the feed roller.

Figure 2:
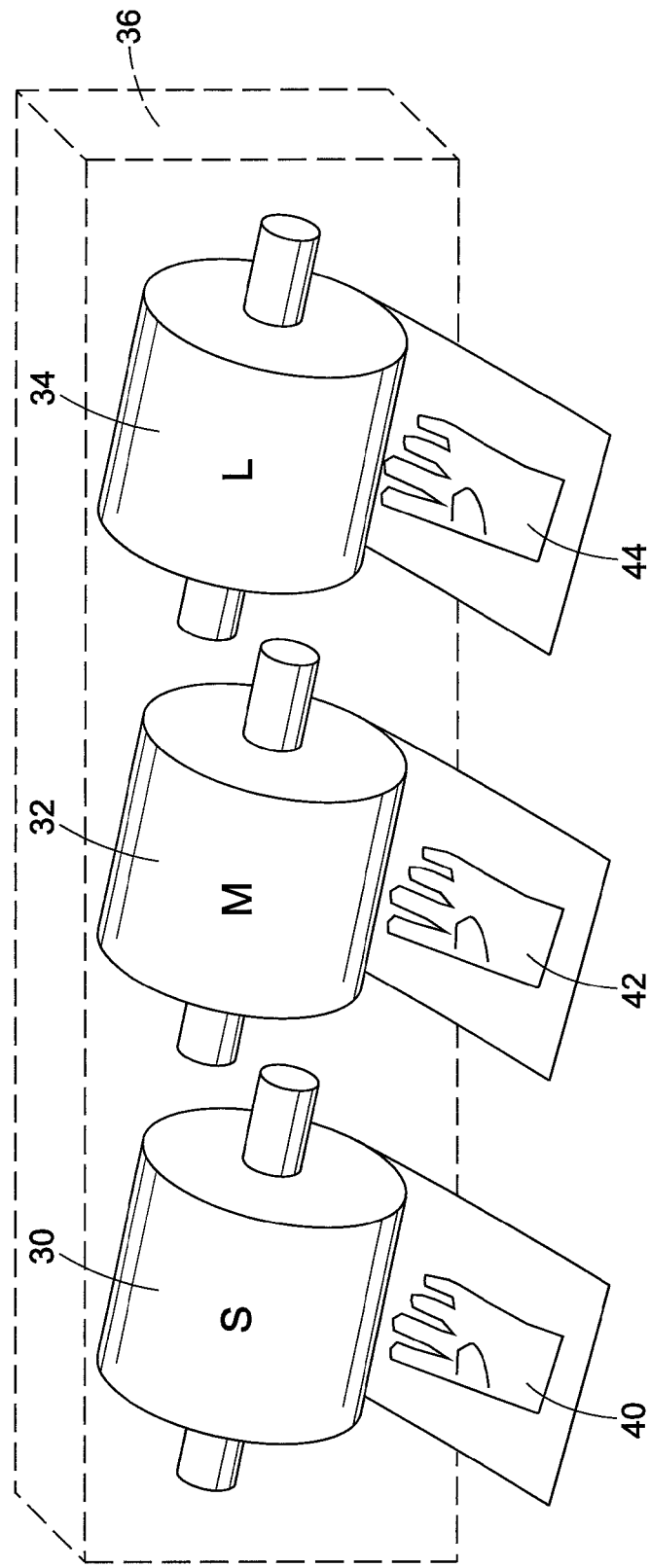
FIG. 2 is a perspective view of a glove dispenser system utilizing three different glove sizes.

Referring now to FIG. 2, alternatively three separate glove rolls 30, 32, 34 can be mounted spaced apart in parallel in a housing 36, wherein first roll 30 contains small sized gloves 40, second roll 32 contains medium sized gloves 42 and third roll 34 contains large size gloves 44. This dispenser itself would also operate as described for FIG. 1.

Figure 3:
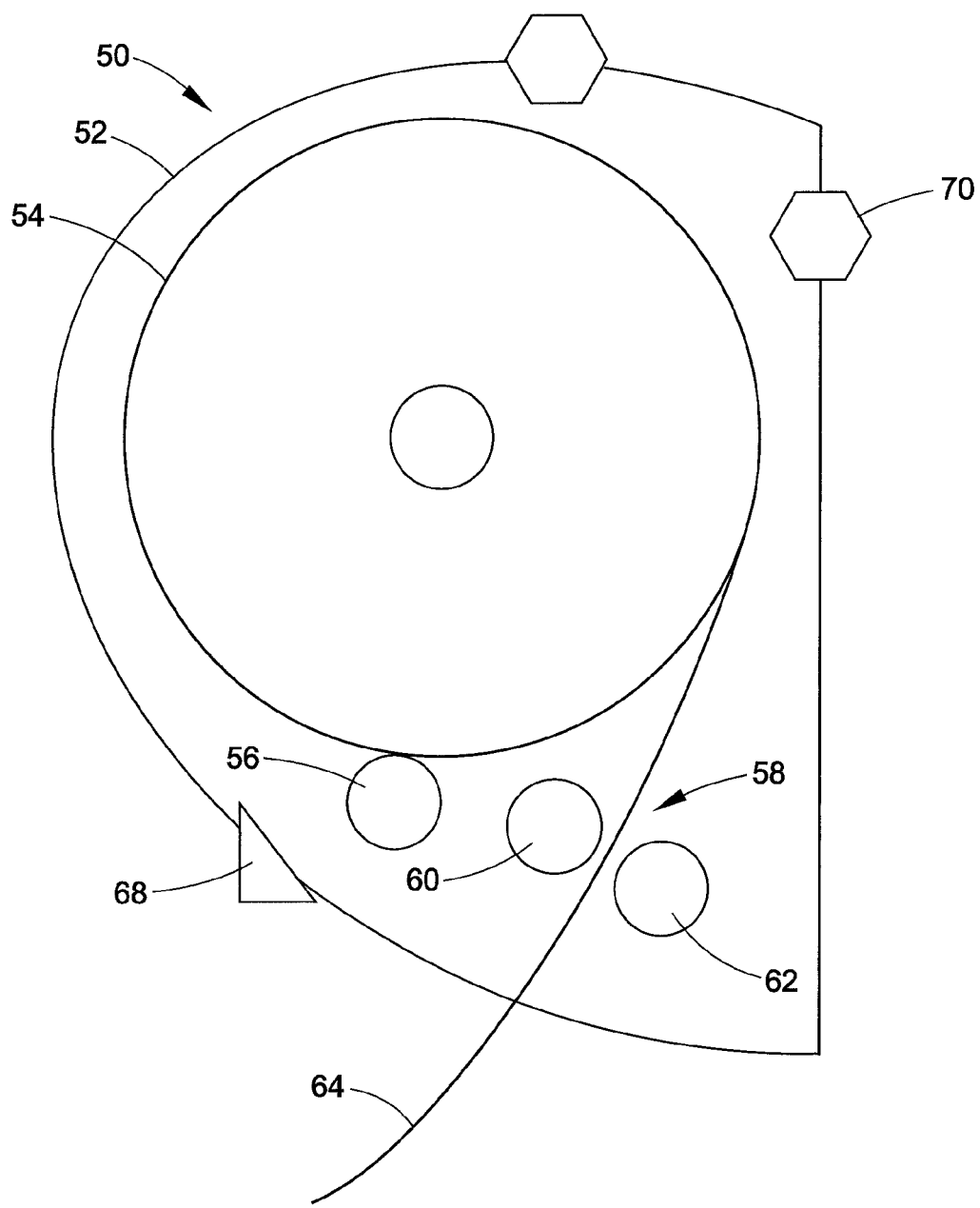
FIG. 3 is a side elevational view of the glove dispenser system of FIG. 1.

Referring now to FIG. 3, in accordance with another embodiment of the disclosure, a housing 50 for the glove dispenser can include a removable or rotatable cover 52 housing a roll 54 of gloves, a pressing bar or roll 56, a lower roller mechanism 58 of a pair of rollers 60, 62 through which the roll material 64 passes, and a proximity sensor 68 mounted at the bottom of the housing. The proximity sensor 68 senses the presence of a user's hand and activates roller mechanism 58 including a rotating engine activated by batteries or electricity. Gloves are thereby disposed at the bottom of the dispenser or roll material 64. The glove roll 54 can be replaced via a side of the cover via hinge springs 70 which allow the cover to open to access the roll 54.

Figure 4:
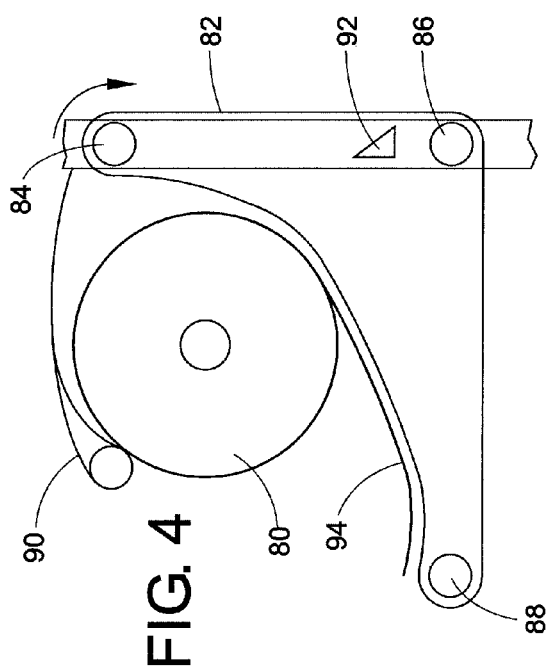
FIG. 4 is a side elevational view of a glove dispenser in accordance with another embodiment of the disclosure.

Referring now to FIG. 4, an alternate embodiment of the disclosure includes a roll 80 of gloves mounted adjacent a vertically oriented band or conveyor belt 82 which is driven by spaced apart rollers 84, 86, 88; and is controlled by pressing bar or roll 90 which presses on the glove roll to maintain contact with the conveyor belt 82. A proximity sensor 92 is placed or located on a side of the housing and activates a motor 96 to dispense glove material 94 by activating the conveyor belt which moves the roll 80 clockwise to dispense the glove sheet 94.

Figure 5B:
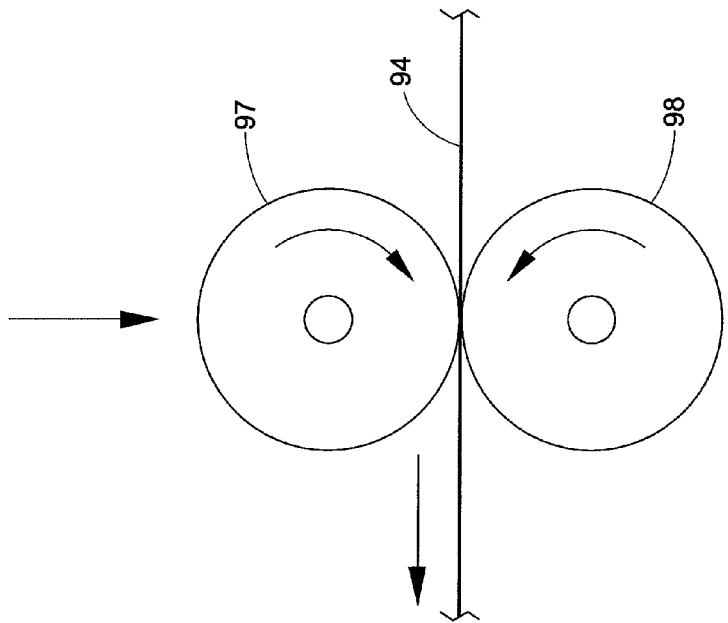
FIG. 5B is a front perspective view of a roller mechanism.
Figure 5A:
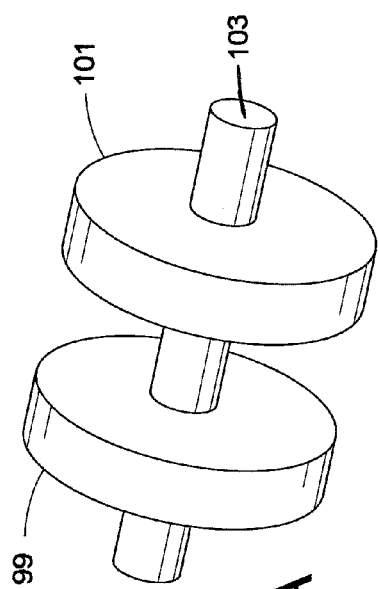
FIG. 5A is a front perspective view of glove rolls with a tensor rod therebetween.

Referring now to FIG. 5A, a roll 80 of gloves can be positioned between two spaced apart rollers 99, 101 on a tensor rod 103 extending between the rollers 99, 101. The rollers 99, 101 can be made of plastic or any suitable material. Referring to FIG. 5B, rollers 97, 98 may be used to apply pressure to the glove roll material 94 as it passes through the mechanism and the material may be manually pulled through the rollers to dispense the gloves.

Figure 6:
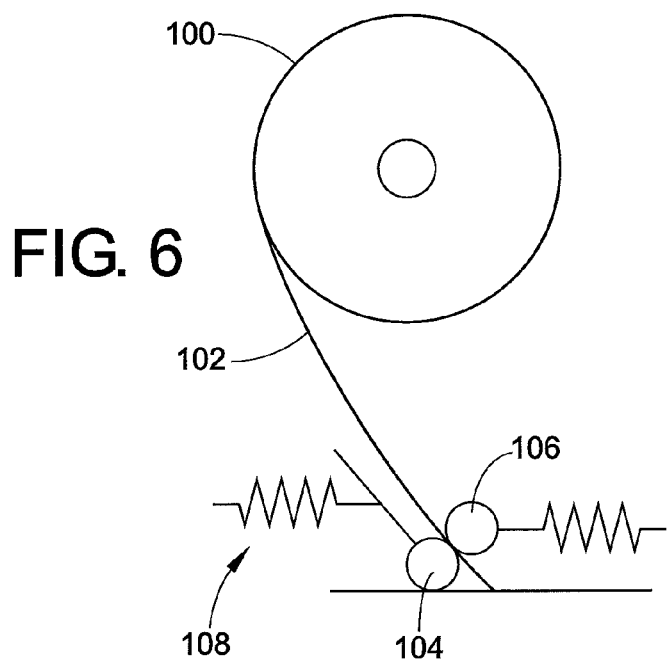
FIG. 6 is a side elevational view of another embodiment of the glove dispenser.

FIG. 6 illustrates another embodiment of the disclosure wherein a roll 100 of glove material 102 extends between pressing rollers 104, 106 which are activated by an electromechanical system 108 such as a battery or motor.

Figure 7:
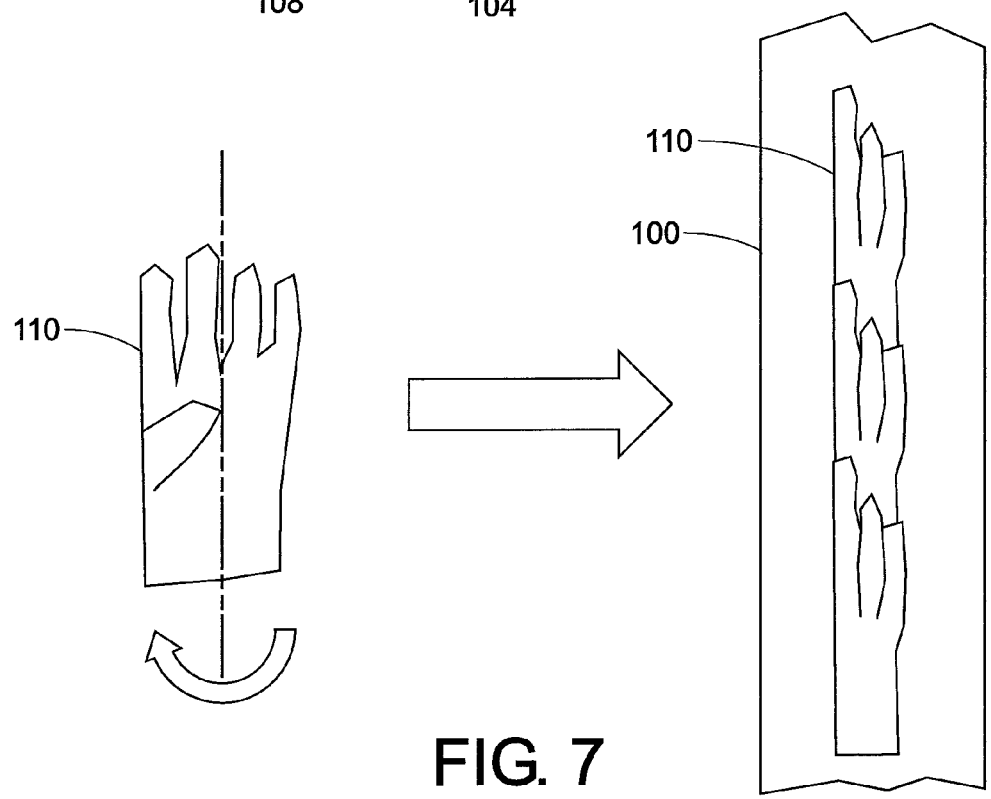
FIG. 7 illustrates another embodiment of a glove dispenser with gloves folded in half.

Referring to FIG. 7, in an alternate embodiment, the roll 100 of gloves may include gloves 110 which are folded in half. The folded gloves are stored or placed on rolls much like the gloves discussed for FIGS. 1-6.

Figure 8:
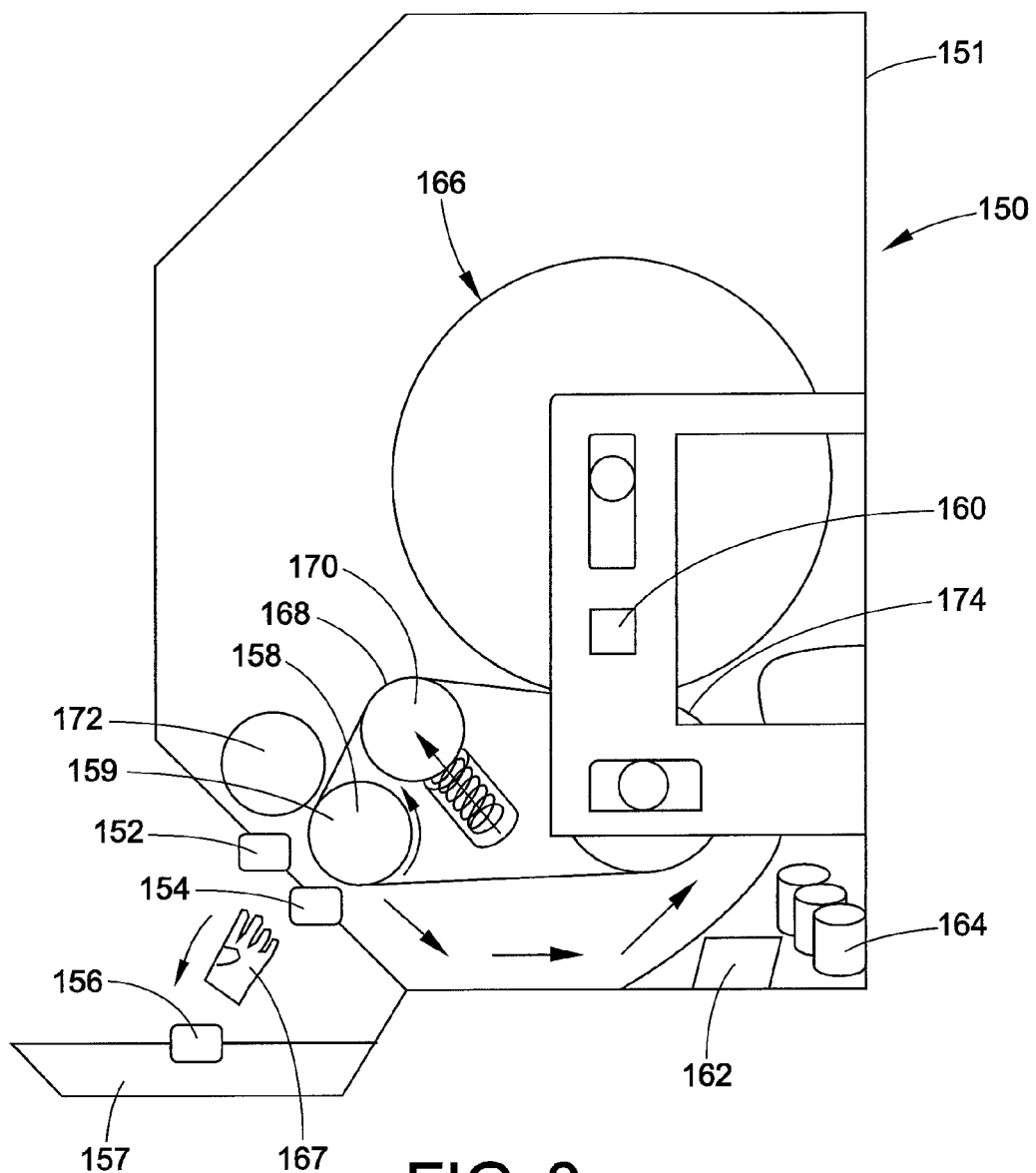
FIG. 8 is a side elevational view in cross section of a glove dispenser in accordance with another embodiment of the disclosure.
Figure 9:
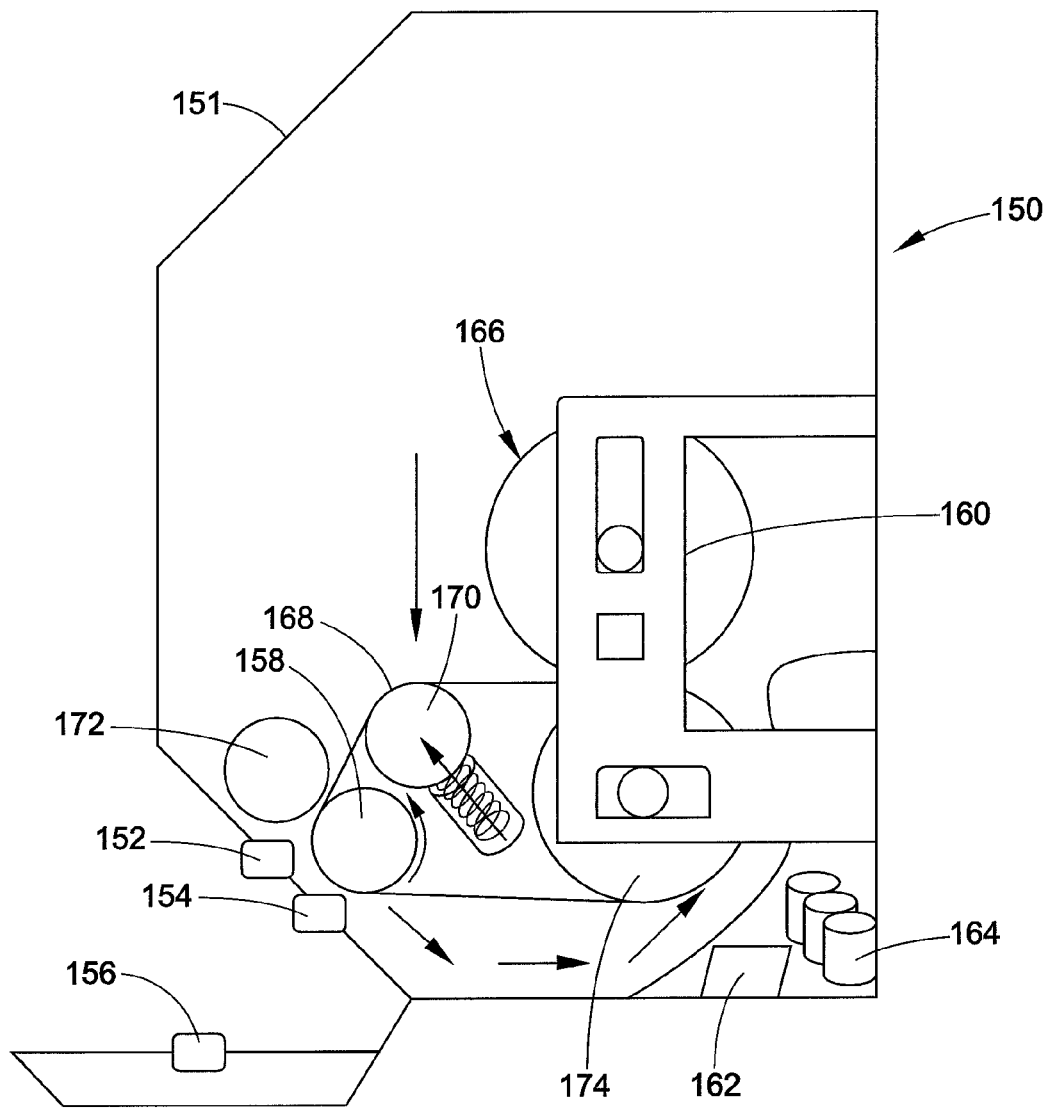
FIG. 9 is a side elevational view in cross section of a glove dispenser of FIG. 8 showing a less full glove roll.

Referring now to FIGS. 8 and 9, another embodiment of the disclosure is illustrated. A glove dispenser assembly 150 includes a housing 151, a glove sensor 152, a proximity sensor 154, a glove tray detector 156, a glove tray 157, a motor rotor/speed sensor 158, a motor 159, an empty sensor 160, internal electronics 162 for operating the motor, batteries 164 for operating the electronics, a glove roll 166 containing gloves 167, and a take-up roll 174.

The glove sensor 152 is used to detect that a set of gloves 167 has been dispensed from glove roll 166. Glove tray detector 156 detects a glove has been dispensed into the tray 175. Paper or roll material 168 moves over or around rollers 170, 172 to the take-up roll 174.

The glove sensor 152 is preferably an infrared sensor. Proximity sensor 154 is used to detect a human user's hand within 5 to 10 cm range. The proximity sensor 154 is preferably a capacitive sensor or an infrared sensor.

The empty sensor 160 is used so that the dispenser can detect that the glove roll 166 is about to be finished or emptied of glove material. The empty sensor is preferably an optical switch or a mechanical switch. The glove roll 166 lowers between its full or loaded position as seen in FIG. 8 to a less full position shown in FIG. 9 and eventually to an empty position. As the roll lowers it will activate the empty sensor.

The motor 159 moves or rotates the glove roll 166. The motor preferably is a standard DC motor with feedback or a stepper motor. The motor rotor/sensor 158 detects if the motor 159 is moving and the rotation that occurs. The motor sensor 158 is preferably an optical sensor or a hall sensor. The motor sensor also needs to detect that the gloves have been dispensed, stocked, etc. The gloves are dispensed from roll 166 to tray 157 after which the paper 168 then rolls onto take-up roll 174.

The batteries 164 used to operate the electronics for powering the motor can be standard 1.5V alkaline batteries (i.e., for a 6V-4V system). There can also be provided a method for sensing battery current and battery voltage to determine a state of charge.

According to another embodiment of the disclosure shown in FIGS. 10-13, a glove dispenser 200 has a case or housing 202 which is preferably formed by two laterally spaced apart walls or side plates 204, 206 and a cover 201 extending over the housing. Two rolls 208, 212 are rotatably mounted within the housing, where each roll is sustained by a roll holder. Specifically, a glove roll holder 210 holds a glove roll 208 holding roll material or paper 209 with gloves 211 removably secured thereon and a paper roll holder 214 holds a paper take-up roll 212 below glove roll holder 210 for holding paper remnants 213. There is a tensor rod 216 between the two rolls and a tensor holder 218 formed on both plates 204, 206 for holding the tensor rod.

The device also has a proximity sensor 220 mounted below rolls 208, 212. A line counter sensor 222 is preferably located on the roll tensor rod 216 in order to count consistently each line in the paper 209 (see FIG. 11). Two engines or motors 224, 226 for rotating rolls 208, 212 respectively, and an area for batteries 228, are enclosed by a front door or plastic cover 201 with hinges and a lock (not shown).

Figure 10:
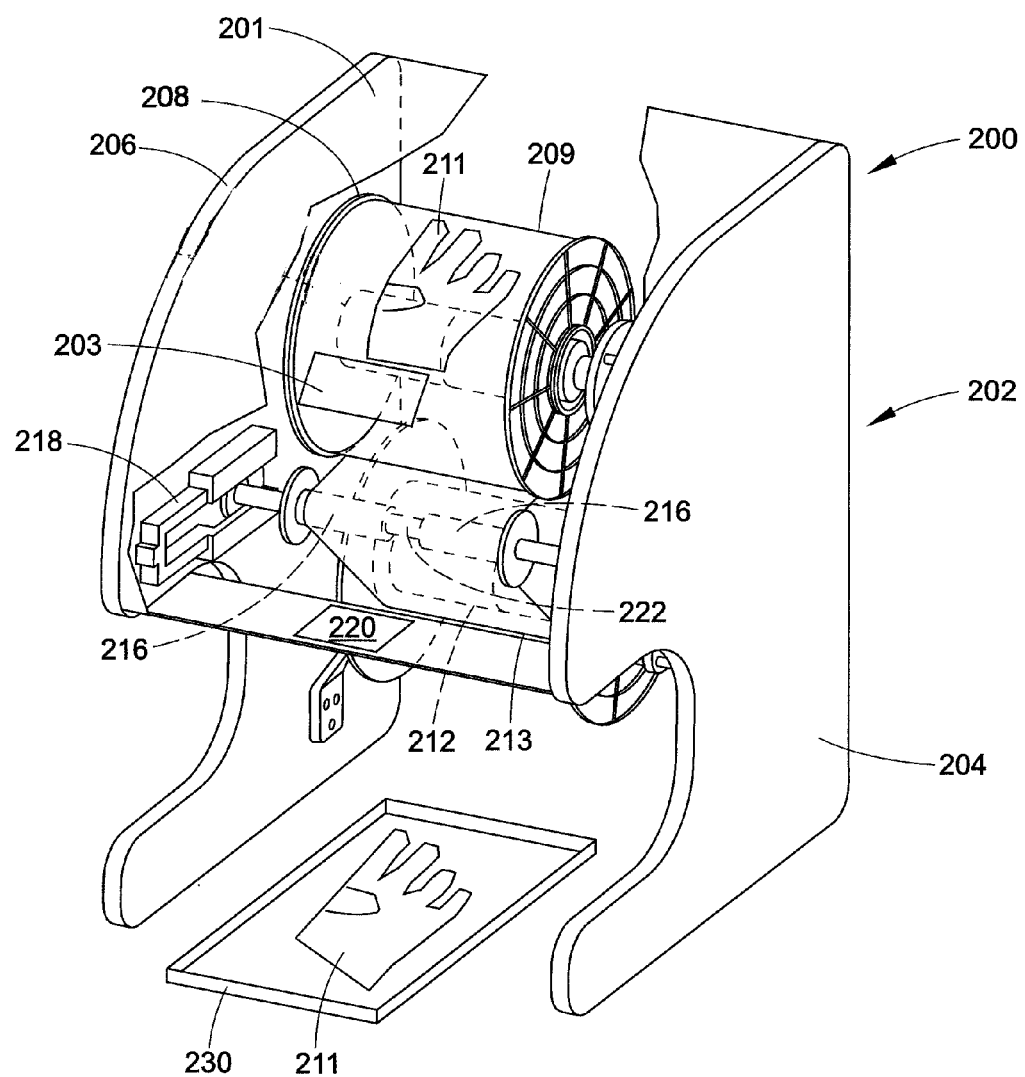
FIG. 10 is a perspective view of a glove dispenser in accordance with another embodiment of the disclosure.
Figure 11:
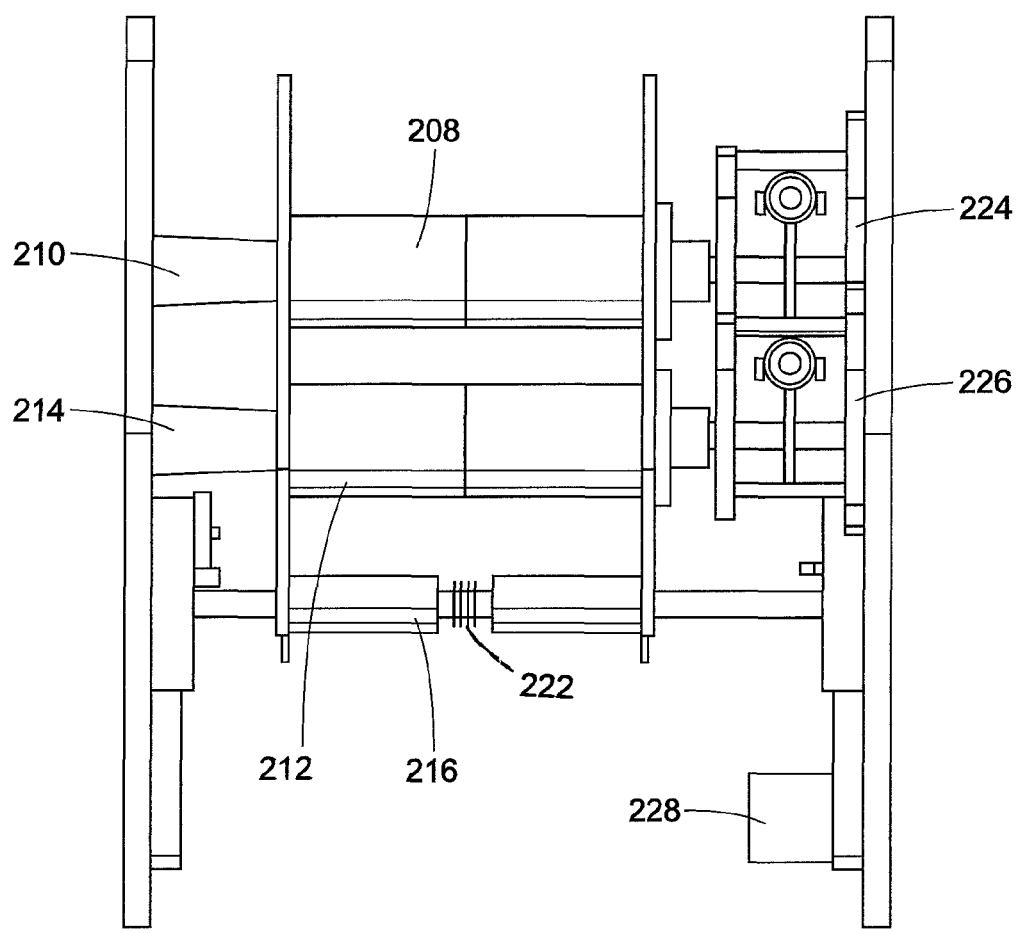
FIG. 11 is a top plan view of the glove dispenser of FIG. 10.
Figure 12:
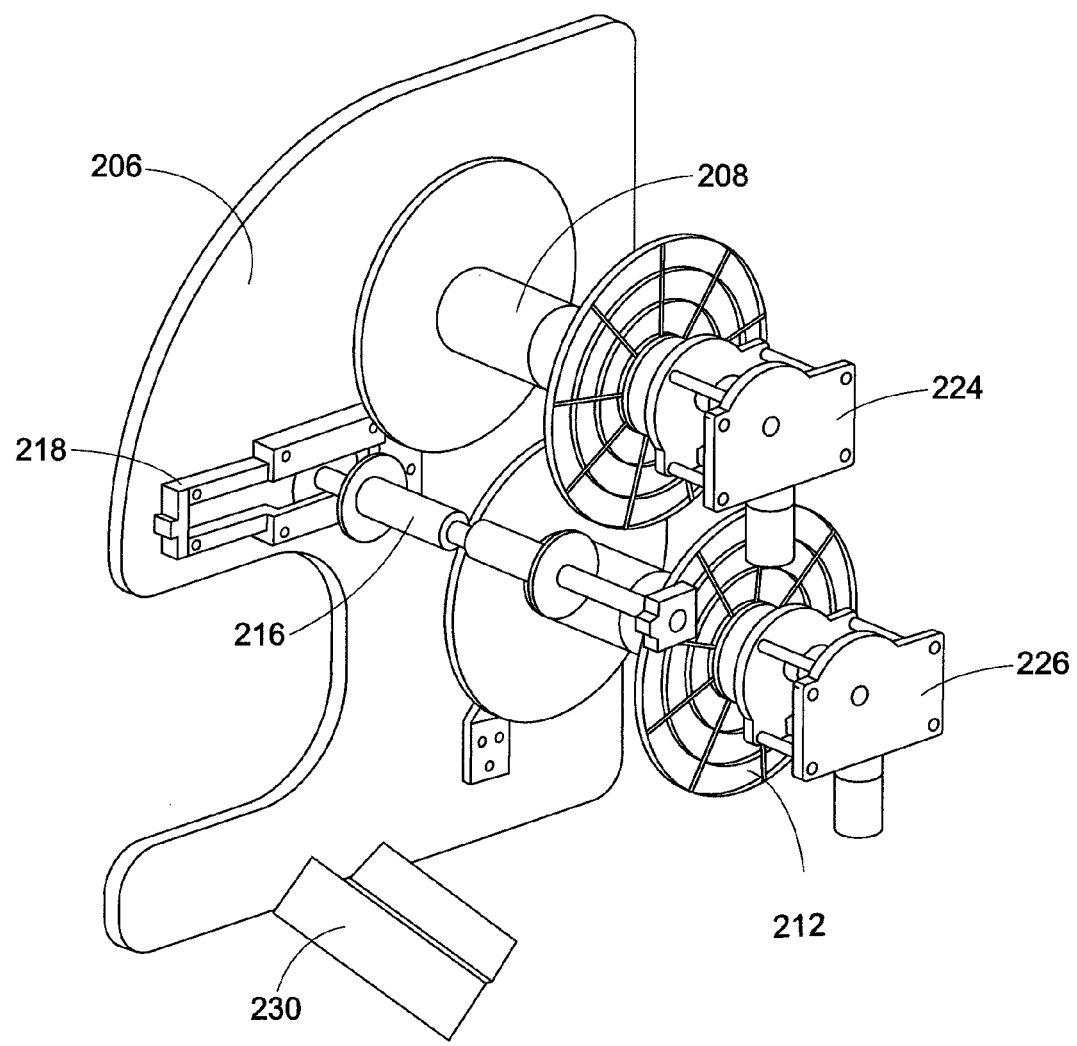
FIG. 12 is a right side partial perspective view of the glove dispenser of FIG. 10.
Figure 13:
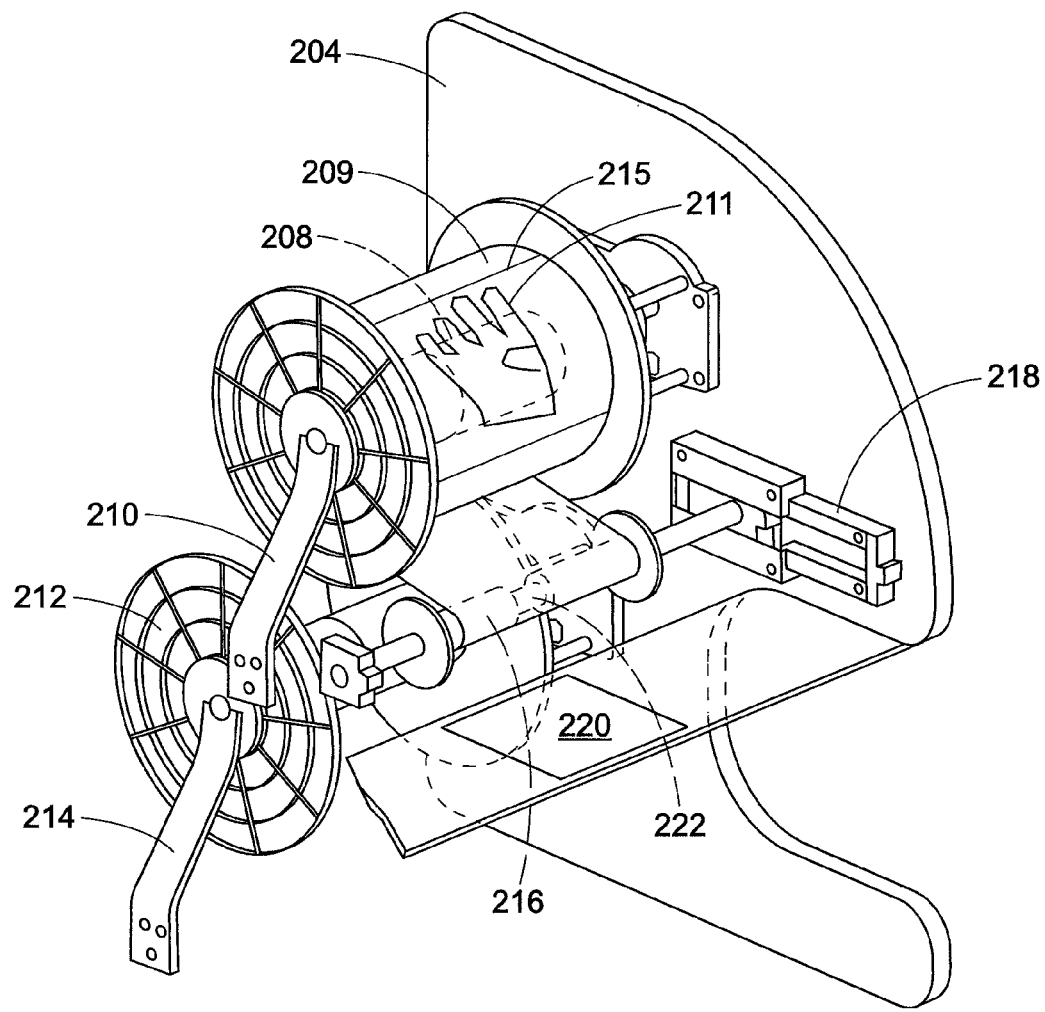
FIG. 13 is a left side partial perspective view of the glove dispenser of FIG. 11.

Referring to FIG. 10, an electronic control board 203 which can be located adjacent cover 201 is used to drive the electric rotation engine and measure all of the sensors to ensure that they react accordingly. The electronic control board 203 also provides all indicators to the user about the status of the glove dispensing process as well as the quantity of the remaining gloves.

The case or housing 202 is preferably made from plastic and is easy to clean and disinfect with wipes. The glove dispenser mechanism has two rolls mounted on roll holders 210, 214 positioned one above the other (see FIG. 13). The top roll 208 contains a prepackaged paper roll 209 with gloves 211, while the bottom take-up roll 212 collects the paper remnants 213 after the gloves are dispensed. The paper remnants are eventually disposed during replacement of the rolls.

The roll tensor 216 between the rolls controls the rotation and dynamics between both rolls as the roll material 209 passes from roll 208 over the tensor rod 216 and becomes paper remnants 213 rolled onto take-up roll 212. During the dispensing process, and after the gloves 211 are released from roll 208 and are dispensed onto tray 230, the paper remnants 213 moves to the lower take-up roll 212. The rolls 208, 212 are each controlled and rotated by engines or motors 224, 226 respectively, that in turn are activated by proximity sensor 220. The proximity sensor 220 detects the presence of a hand of an operator. The paper roll material 209 has a premarked line 215 (FIG. 13) that facilitates the counting of the gloves that have been dispensed by line counter sensor 222. The line counter sensor 222 activates a pilot light when about ten gloves are left on the glove roll 208 in the glove dispenser to indicate that the roll 208 will need to be replaced, and the paper collector take-up roll 212 is then disposed. Each glove roll 208 preferably has about two hundred gloves 211. However, other numbers of gloves are contemplated by the disclosure.

The exemplary embodiment has been described with reference to the preferred embodiments. Obviously, modifications and alterations will occur to others upon reading and understanding the preceding detailed description. It is intended that the exemplary embodiment be construed as including all such modifications and alterations.

The invention claimed is:

1. A glove dispenser assembly comprising:
a housing;
a plurality of gloves;
a glove roll adapted to hold said gloves mounted within said housing;
said glove roll comprises roll material wound thereon, wherein said gloves are removably secured to said roll material wherein said roll material has a plurality of pre-marked lines formed between said gloves for counting said gloves wherein said plurality of pre-marked lines extend from one edge of said glove roll to an opposite edge of said glove roll;
a glove tray positioned at a bottom portion of said housing for receiving said gloves from said glove roll and a line counter sensor for counting said pre-marked lines on said roll material;
a first motor for driving said glove roll;
a proximity sensor for detecting a user's hand for activating said glove roll;
a take-up roll positioned below said glove roll and a second motor for driving said take-up roll; and
a glove tray detector for sensing a glove dispensed from said glove roll onto said glove tray.

2. The glove dispenser of claim 1, further comprising first and second rollers over which said roll material passes.

3. The glove dispenser of claim 1, further comprising an empty sensor for detecting that the glove roll is substantially empty of said roll material.

4. A glove dispenser comprising:
a housing;
a plurality of gloves;
a glove roll mounted within said housing for holding said gloves comprising a sheet wherein said plurality of gloves are removably secured to said sheet wherein said sheet has a plurality of pre-marked lines formed between said gloves for counting said gloves wherein said plurality of pre-marked lines extend from one edge of said glove roll to an opposite edge of said glove roll;
a first motor for rotating said glove roll;
a take-up roll mounted within said housing and positioned below said glove roll for receiving said sheet;
a second motor for rotating said take-up roll;
a tensor arm for controlling rotation of said glove roll and said take-up roll;
at least one proximity sensor positioned near a lower portion of said housing; and
a glove take-up tray positioned near a lower portion of said housing for receiving said gloves from said glove roll and a line counter sensor for counting said pre-marked lines on said sheet.

5. The glove dispenser of claim 4, further comprising:
a first roll holder mounted to said housing for holding said glove roll and a second roll holder for holding said take-up roll.

6. The glove dispenser of claim 4, further comprising a line counter sensor for indicating a number of gloves left on said glove roll.

7. The glove dispenser of claim 4, further comprising a tensor arm holder for holding said tensor arm.

* * * * *